(12) United States Patent
Chung

(10) Patent No.: US 12,234,444 B2
(45) Date of Patent: Feb. 25, 2025

(54) COMPOSITION FOR PROMOTING THE GROWTH OF LACTIC ACID BACTERIA COMPRISING GROWTH FACTORS

(71) Applicant: CELL BIOTECH CO., LTD., Gimpo-si (KR)

(72) Inventor: Myung Jun Chung, Seoul (KR)

(73) Assignee: CELL BIOTECH CO., LTD., Gimpo-si (KR)

(*) Notice: Subject to any disclaimer, the term of this patent is extended or adjusted under 35 U.S.C. 154(b) by 0 days.

(21) Appl. No.: 18/454,562

(22) Filed: Aug. 23, 2023

(65) Prior Publication Data
US 2023/0392111 A1 Dec. 7, 2023

Related U.S. Application Data

(63) Continuation of application No. 17/108,558, filed on Dec. 1, 2020, now abandoned.

(30) Foreign Application Priority Data

Jan. 2, 2020 (KR) ........................ 10-2020-0000255

(51) Int. Cl.
*C12N 1/20* (2006.01)
(52) U.S. Cl.
CPC ............ *C12N 1/20* (2013.01); *C12N 2500/05* (2013.01); *C12N 2500/34* (2013.01); *C12N 2500/74* (2013.01)
(58) Field of Classification Search
None
See application file for complete search history.

(56) References Cited

U.S. PATENT DOCUMENTS 8,697,055 B2    4/2014  Farmer

FOREIGN PATENT DOCUMENTS

| CN | 1149092 | C |   | 5/2004 |   |
|----|---------|---|---|--------|---|
| CN | 108373984 | A |   | 8/2018 |   |
| CN | 109097306 | A | * | 12/2018 |   |
| CN | 108277178 | B | * | 7/2021 | ........... A23L 33/135 |
| KR | 20020061041 | A |   | 7/2002 |   |
| KR | 20100010557 | A |   | 2/2010 |   |

OTHER PUBLICATIONS

Amrane, A; Prigent Y; "Infuence of yeast extract concentration on batch cultures of Lactobacillus helveticus: growth and production coupling" World Journal of Microbiology & Biotechnology, 14, 529-534, 1998 (Year: 1998).*

Applicant: Cell Biotech Co., Ltd.; European Application No. 20209030; European Search Report dated May 21, 2021; Dated May 12, 2021; 50 pgs.

(Continued)

*Primary Examiner* — David W Berke-Schlessel
(74) *Attorney, Agent, or Firm* — Tarolli, Sundheim, Covell & Tummino LLP

(57) ABSTRACT

The present disclosure relates to a composition for promoting the growth of lactic acid bacteria comprising growth factors, and more particularly, to a composition for promoting the growth of lactic acid bacteria comprising growth factors, the composition being capable of efficiently promoting the growth of various lactic acid bacteria strains.

2 Claims, 4 Drawing Sheets

(56) References Cited

OTHER PUBLICATIONS

Sghir, A., et al., "Continuous Culture slection of bifidobacterial lactobacilli from human faecal samples using fructoologosaccharise as Selective Substrate", Journal of Applied Microbiology 1998, 85, 769-777.
Lactobacilli MRS Broth (NCM0079); Technical Specification Sheet; Neogen Culture Media (Year: 2021).
Non-Final Office Action for U.S. Appl. No. 17/108,558 dated Dec. 23, 2022.
Final Office Action for U.S. Appl. No. 17/108,558 dated May 23, 2023.

* cited by examiner

[FIG. 1]
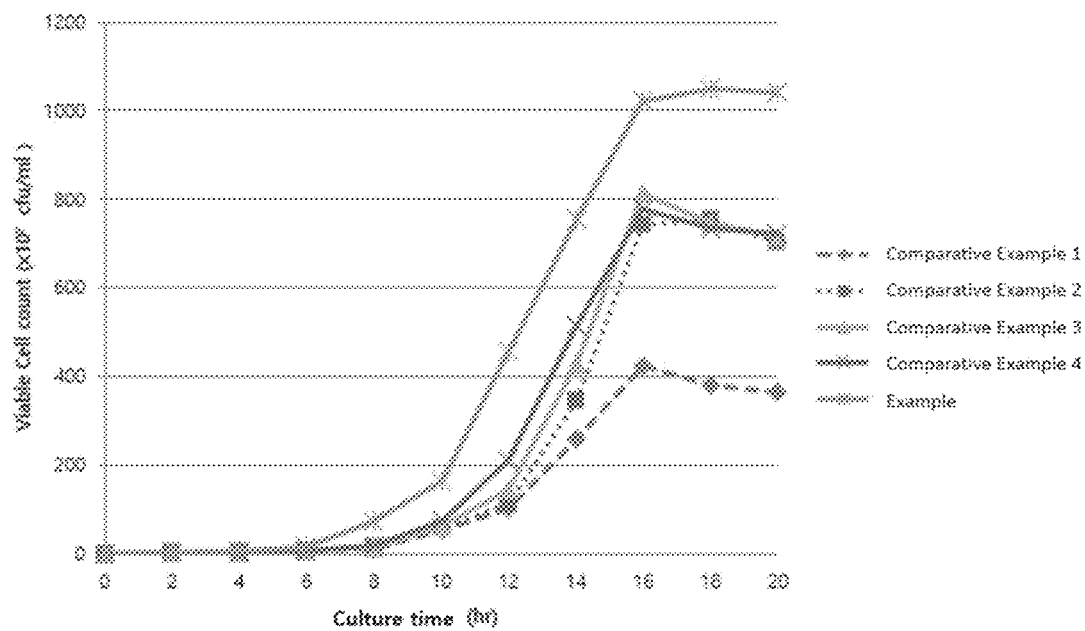

[FIG. 2]
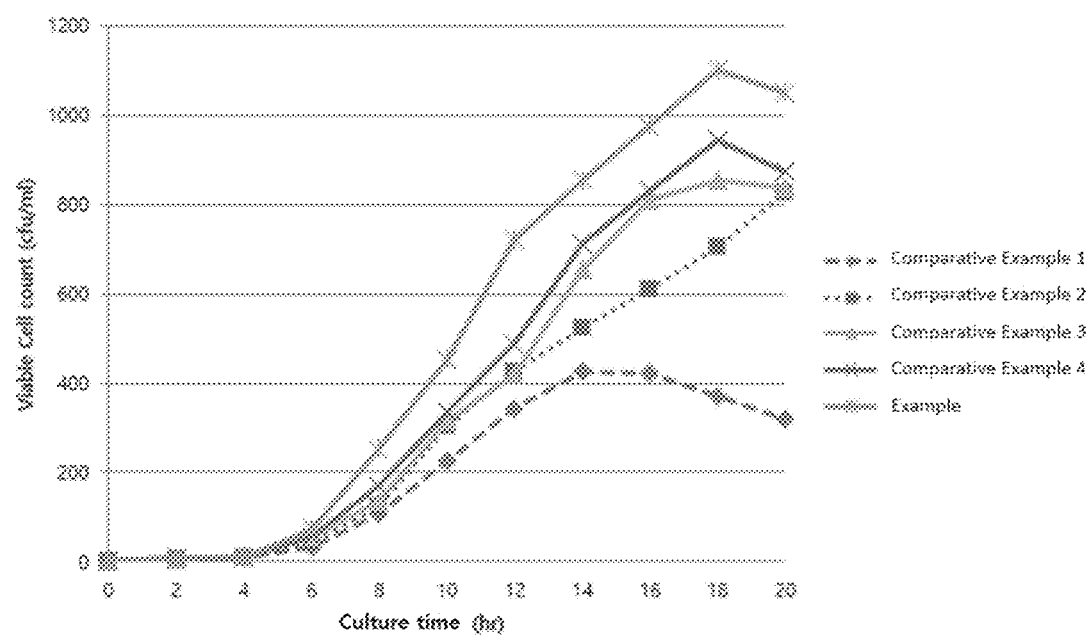

[FIG. 3]
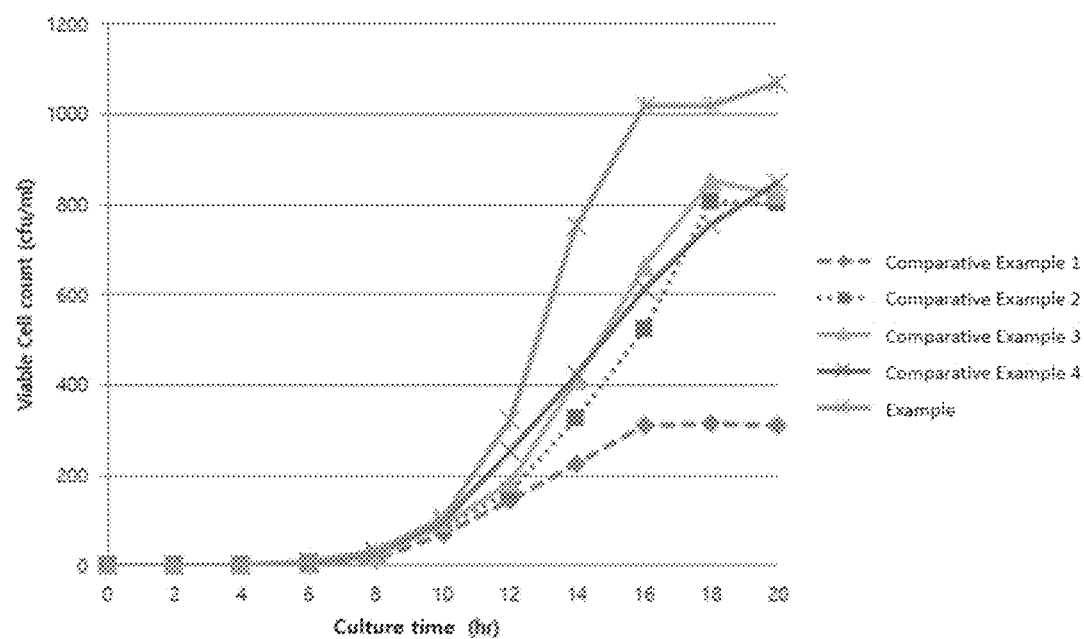

[FIG. 4]
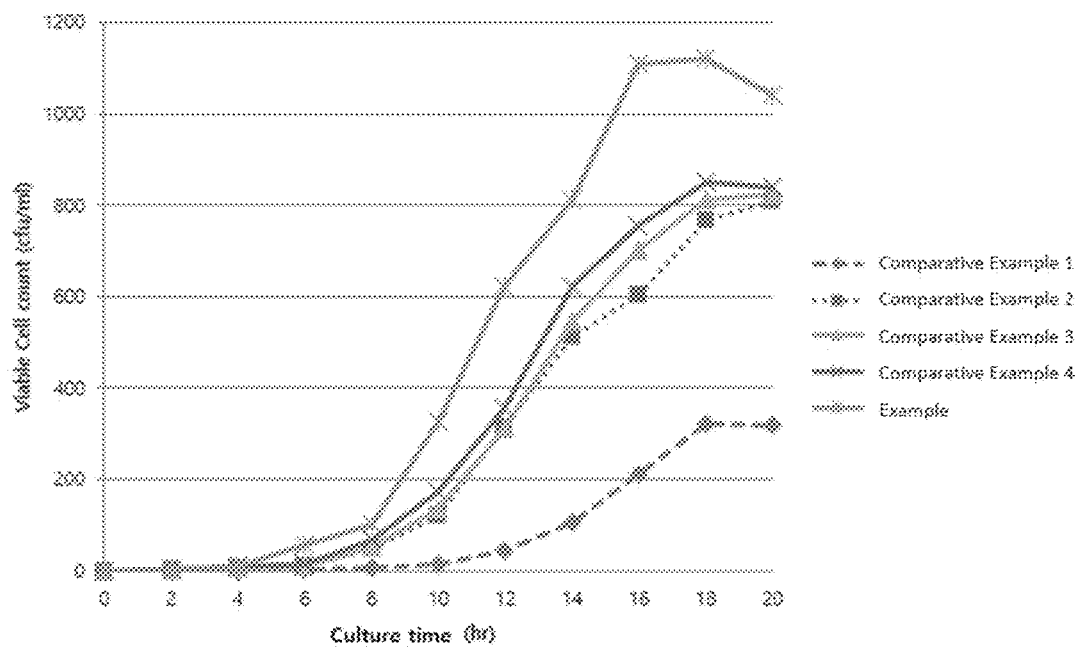

COMPOSITION FOR PROMOTING THE GROWTH OF LACTIC ACID BACTERIA COMPRISING GROWTH FACTORS

CROSS-REFERENCE TO RELATED APPLICATION(S)

This application a continuation of U.S. patent application Ser. No. 17/108,558, filed on Dec. 1, 2020 entitled "COMPOSITION FOR PROMOTING THE GROWTH OF LACTIC ACID BACTERIA COMPRISING GROWTH FACTORS", which claims the priority and benefit of Korean Patent Application No. 10-2020-0000255, filed on Jan. 2, 2020, the disclosure of which is incorporated herein by reference in its entirety.

BACKGROUND

Technical Field

The present disclosure relates to a composition for promoting the growth of lactic acid bacteria comprising growth factors, and more particularly, to the composition being capable of efficiently promoting the growth of various lactic acid bacteria strains.

Description of the Related Art

Due to increased demand for probiotics, probiotic lactic acid bacteria have become the second largest market after red ginseng among health functional foods in the health functional food market, and along with this, interest in prebiotics, which promote the growth of lactic acid bacteria, has also increased. However, currently commercially available prebiotics are limited to fructooligosaccharides, and the effects thereof have not been scientifically proven and are also uncertain. Accordingly, the development of scientifically proven compositions for promoting the growth of lactic acid bacteria is necessarily required, and the effects thereof also need to be reliably identified.

Although components or substances that promote the growth of each type of lactic acid bacteria are known, studies on substances or compositions that can be applied universally to various strains are comprehensive studies that require a long time, much effort, a large cost and a lot of manpower, and a study environment, facilities and systems, which satisfy these requirements, are required for these studies.

The growth curve of microorganisms can be largely divided into the following four sequential phases: a lag phase in which microorganisms adapt to the environment and express enzymes necessary for cell division; an exponential phase in which cell division is promoted and microorganisms proliferate; a stationary phase in which the cell number remains constant without further increase; and a death phase in which the cell number decreases due to cell death.

It could be confirmed that a composition for promoting the growth of lactic acid bacteria according to the present disclosure could be applied to various lactic acid bacteria and exhibited a clear effect on stable maintenance of the number of lactic acid bacteria by reducing the duration of the lag phase, increasing the number of lactic acid bacteria in the exponential phase, and increasing the duration of the stationary phase. This effect means that the composition according to the present disclosure is of great help in allowing ingested probiotics to effectively settle in gut and to maintain their function during growth and retention in the gut. In addition, this effect can explain that the composition of the present disclosure comprises a proven growth factor that promotes the growth of lactic acid bacteria, unlike conventional prebiotics composed only of sugars. It is expected that an optimal mixture composition comprising a carbon source and a nitrogen source according to the present disclosure can be used universally as a composition for promoting the growth of various lactic acid bacteria.

SUMMARY

The present inventors have conducted studies and made efforts to develop a composition capable of efficiently promoting the growth of various lactic acid bacteria strains. As a result, the present inventors have developed a composition for promoting the growth of lactic acid bacteria comprising growth factors, which is capable of promoting the growth of various lactic acid bacteria strains, and have experimentally proved and confirmed that the composition efficiently promotes the growth of lactic acid bacteria, thereby completing the present disclosure.

Therefore, an object of the present disclosure is to provide a composition for promoting the growth of lactic acid bacteria, the composition comprising, as growth factors: a carbon source comprising glucose and fructooligosaccharide; and a nitrogen source comprising yeast extract and isolated soy protein.

Other objects and advantages of the present disclosure will be illustrated in more detail by the following detailed description, the appended claims and the accompanying drawings.

According to one aspect of the present disclosure, the present disclosure provides a composition for promoting the growth of lactic acid bacteria, the composition comprising: a carbon source comprising glucose and fructooligosaccharide; and a nitrogen source comprising yeast extract and isolated soy protein.

As used herein, the term "growth factors" refers to compounds, including the above-described carbon source and nitrogen source, which act as substrates for lactic acid bacteria of the present disclosure and promote the growth of the lactic acid bacteria.

In one embodiment of the present disclosure, the glucose may be comprised in an amount of 20 to 40 wt %, preferably 40 wt %, based on 100 wt % of the composition for promoting the growth of lactic acid bacteria. In addition, the fructooligosaccharide may be comprised in an amount of 20 to 40 wt %, preferably 40 wt %, based on 100 wt % of the composition for promoting the growth of lactic acid bacteria. Furthermore, the yeast extract may be comprised in an amount of 10 to 30 wt %, preferably 15 wt %, based on 100 wt % of the composition for promoting the growth of lactic acid bacteria. Additionally, the isolated soy protein may be comprised in an amount of 5 to 30 wt %, preferably 5 wt %, based on 100 wt % of the composition for promoting the growth of lactic acid bacteria.

In one embodiment of the present disclosure, the weight ratio between the glucose and the fructooligosaccharide in the carbon source may be 1:3 to 3:1, preferably 1:1.

In one embodiment of the present disclosure, the weight ratio between the yeast extract and the isolated soy protein in the nitrogen source may be 1:3 to 3:1, preferably 3:1.

The lactic acid bacteria of the present disclosure may be probiotic lactic acid bacteria in the sense that when they are administered in vivo, they settle in the gut and have a beneficial synergistic effect with the gut microbiota.

In one embodiment of the present disclosure, the lactic acid bacteria that are used in the present disclosure may be one or more lactic acid bacteria selected from the group consisting of lactic acid bacteria of the genus *Lactobacillus*, lactic acid bacteria of the genus *Bifidobacterium*, lactic acid bacteria of the genus *Streptococcus*, and lactic acid bacteria of the genus *Pediococcus*.

In another embodiment of the present disclosure, the lactic acid bacteria of the genus *Lactobacillus* may be one or more lactic acid bacteria selected from the group consisting of *Lactobacillus casei*, *Lactobacillus plantarum* and *Lactobacillus rhamnosus*. The *Lactobacillus casei* is preferably *Lactobacillus casei* CBT-LC5, more preferably *Lactobacillus casei* CBT-LC5 (accession number: KCTC 12398BP). The *Lactobacillus plantarum* is preferably *Lactobacillus plantarum* CBT-LP3, more preferably *Lactobacillus plantarum* CBT-LP3 (accession number: KCTC 10782BP). The *Lactobacillus rhamnosus* is preferably *Lactobacillus rhamnosus* CBT-LR5, more preferably *Lactobacillus rhamnosus* CBT-LR5 (accession number: KCTC 12202BP). However, the present disclosure is not limited thereto.

In still another embodiment of the present disclosure, the lactic acid bacteria of the genus *Bifidobacterium* may be one or more lactic acid bacteria selected from the group consisting of *Bifidobacterium longum*, *Bifidobacterium lactis* and *Bifidobacterium bifidum*. The *Bifidobacterium longum* is preferably *Bifidobacterium longum* CBT-BG7, more preferably *Bifidobacterium longum* CBT-BG7 (accession number: KCTC 12200BP). The *Bifidobacterium lactis* is preferably *Bifidobacterium lactis* CBT-BL3, more preferably *Bifidobacterium lactis* CBT-BL3 (accession number: KCTC 11904BP). The *Bifidobacterium bifidum* is preferably *Bifidobacterium bifidum* CBT-BF3, more preferably *Bifidobacterium bifidum* CBT-BF3 (accession number: KCTC 12199BP). However, the present disclosure is not limited thereto.

In yet another embodiment of the present disclosure, the lactic acid bacteria of the genus *Streptococcus* may be *Streptococcus thermophilus*. The *Streptococcus thermophilus* is preferably *Streptococcus thermophilus* CBT-ST3, more preferably *Streptococcus thermophilus* CBT-ST3 (accession number: KCTC 11870BP). However, the present disclosure is not limited thereto.

In still yet another embodiment of the present disclosure, the lactic acid bacteria of the genus *Pediococcus* may be *Pediococcus pentosaceus*. The *Pediococcus pentosaceus* is preferably *Pediococcus pentosaceus* CBT-SL4, more preferably *Pediococcus pentosaceus* CBT-SL4 (accession number: 10297BP), but the present disclosure is not limited thereto.

BRIEF DESCRIPTION OF THE DRAWINGS

FIG. 1 shows the results of evaluating the effect of treatment with a composition for promoting the growth of lactic acid bacteria comprising growth factors on the growth of *Lactobacillus casei* CBT LC5.

FIG. 2 shows the results of evaluating the effect of treatment with the composition for promoting the growth of lactic acid bacteria comprising growth factors on the growth of *Bifidobacterium longum* CBT BG7.

FIG. 3 shows the results of evaluating the effect of treatment with the composition for promoting the growth of lactic acid bacteria comprising growth factors on the growth of *Bifidobacterium bifidum* CBT-BF3.

FIG. 4 shows the results of evaluating the effect of treatment with the composition for promoting the growth of lactic acid bacteria comprising growth factors on the growth of *Streptococcus thermophilus* CBT-ST3.

DESCRIPTION OF SPECIFIC EMBODIMENTS

The specific embodiments described herein are representative of preferred embodiments or examples of the present disclosure, and thus the scope of the present disclosure is not limited thereto. It will be apparent to those skilled in the art that modifications and other uses of the present disclosure do not depart from the scope of the present disclosure as defined in the appended claims.

EXAMPLES

Experimental Methods

Example: Selection of Optimal Composition

To promote the growth of non-specific various types of lactic acid bacteria, an optimal mixture composition was determined by culturing each of the following strains using each component, ratio and composition and measuring the viable cell count of each of the strains: *Lactobacillus casei* CBT-LC5 (accession number: KCTC 12398BP), *Lactobacillus plantarum* CBT-LP3 (accession number: KCTC 10782BP), *Lactobacillus rhamnosus* CBT-LR5 (accession number: KCTC 12202BP), *Bifidobacterium longum* CBT-BG7 (accession number: KCTC 12200BP), *Bifidobacterium lactis* CBT-BL3 (accession number: KCTC 11904BP), *Bifidobacterium bifidum* CBT-BF3 (accession number: KCTC 12199BP), *Streptococcus thermophilus* CBT-ST3 (accession number: KCTC 11870BP), and *Pediococcus pentosaceus* CBT-SL4 (accession number: KCTC 10297BP). Starter cultures were prepared using BL broth.

Experimental Example 1: Experiment of Selection of Carbon Source

As shown in Table 1 below, 2 parts by weight of each carbon source was added to 100 parts by weight of BL broth, thereby preparing media.

TABLE 1

| Strain name | Control (BL broth) | Glucose | Fructose | Refined sugar | Lactose | Fructo-oligosaccharid |
|---|---|---|---|---|---|---|
| *Lactobacillus casei* CBT LC5 | 0% | 2% | 2% | 2% | 2% | 2% |
| *Lactobacillus plantarum* CBT LP3 | 0% | 2% | 2% | 2% | 2% | 2% |
| *Lactobacillus rhamnosus* CBT LR5 | 0% | 2% | 2% | 2% | 2% | 2% |
| *Bifidobacterium longum* CBT BG7 | 0% | 2% | 2% | 2% | 2% | 2% |
| *Bifidobacterium lactis* CBT BL3 | 0% | 2% | 2% | 2% | 2% | 2% |
| *Bifidobacterium bifidum* CBT BF3 | 0% | 2% | 2% | 2% | 2% | 2% |

TABLE 1-continued

| Strain name | Control (BL broth) | Glucose | Fructose | Refined sugar | Lactose | Fructo-oligosaccharid |
|---|---|---|---|---|---|---|
| *Streptococcus thermophilus* CBT ST3 | 0% | 2% | 2% | 2% | 2% | 2% |
| *Pediococcus pentosaceus* CBT SL4 | 0% | 2% | 2% | 2% | 2% | 2% |

0.1 to 1 part by weight of each of the starter cultures was inoculated into 100 parts by weight of each prepared medium, and then cultured for 20 hours while the pH was maintained at about 5.0 to 6.5. Next, the viable cell count of each culture was measured, and the results of the measurement are summarized in Table 2 below. As a result, it was confirmed that culture with glucose or fructooligosaccharide exhibited an excellent effect on the growth of the lactic acid bacteria. Thus, glucose or fructooligosaccharide was selected as a carbon source for a subsequent experiment (Table 2).

TABLE 2

(unit: $\times 10^7$ cfu/ml)

| Strain name | Control (BL broth) | Glucose | Fructose | Refined sugar | Lactose | Fructo-oligosaccharide |
|---|---|---|---|---|---|---|
| *Lactobacillus casei* CBT LC5 | 348 | 650 | 408 | 482 | 405 | 615 |
| *Lactobacillus plantarum* CBT LP3 | 318 | 613 | 452 | 427 | 550 | 616 |
| *Lactobacillus rhamnosus* CBT LR5 | 212 | 615 | 486 | 425 | 405 | 580 |
| *Bifidobacterium longum* CBT BG7 | 363 | 612 | 405 | 464 | 456 | 570 |
| *Bifidobacterium lactis* CBT BL3 | 410 | 770 | 522 | 472 | 420 | 715 |
| *Bifidobacterium bifidum* CBT BF3 | 306 | 640 | 434 | 325 | 460 | 660 |
| *Streptococcus thermophilus* CBT ST3 | 280 | 620 | 402 | 504 | 450 | 640 |
| *Pediococcus pentosaceus* CBT SL4 | 322 | 650 | 550 | 580 | 520 | 702 |

Experimental Example 2: Experiment for Combination of Carbon Sources

As shown in Table 3 below, glucose and fructooligosaccharide were mixed together at the indicated ratios, and then 2 parts by weight of each mixture was added to 100 parts by weight of BL broth, thereby preparing media.

TABLE 3

| Strain name | Control (BL broth) | 1:1 50%:50% | 1:2 33%:67% | 1:3 25%:75% | 2:1 67%:33% | 3:1 75%:25% |
|---|---|---|---|---|---|---|
| *Lactobacillus casei* CBT LC5 | 0% | 2% | 2% | 2% | 2% | 2% |
| *Lactobacillus plantarum* CBT LP3 | 0% | 2% | 2% | 2% | 2% | 2% |
| *Lactobacillus rhamnosus* CBT LR5 | 0% | 2% | 2% | 2% | 2% | 2% |
| *Bifidobacterium longum* CBT BG7 | 0% | 2% | 2% | 2% | 2% | 2% |
| *Bifidobacterium lactis* CBT BL3 | 0% | 2% | 2% | 2% | 2% | 2% |
| *Bifidobacterium bifidum* CBT BF3 | 0% | 2% | 2% | 2% | 2% | 2% |
| *Streptococcus thermophilus* CBT ST3 | 0% | 2% | 2% | 2% | 2% | 2% |
| *Pediococcus pentosaceus* CBT SL4 | 0% | 2% | 2% | 2% | 2% | 2% |

0.1 to 1 part by weight of each starter culture was inoculated into 100 parts by weight of each prepared medium, and then cultured for 20 hours while the pH was maintained at about 5.0 to 6.5. Next, the viable cell count of each culture was measured, and the results of the measurement are summarized in Table 4 below. As a result, it was confirmed that culture with glucose and fructooligosaccharide at the same mixing ratio (50%:50%) exhibited a better effect on the growth of the lactic acid bacteria than culture at the other mixing ratios. Thus, the mixing ratio of 50:50 was selected as a mixing ratio for a subsequent experiment (Table 4).

TABLE 4

(unit: ×10⁷ cfu/ml)

| Strain name | Control (BL broth) | 1:1 50%:50% | 1:2 33%:67% | 1:3 25%:75% | 2:1 67%:33% | 3:1 75%:25% |
|---|---|---|---|---|---|---|
| *Lactobacillus casei* CBT LC5 | 356 | 725 | 616 | 608 | 620 | 618 |
| *Lactobacillus plantarum* CBT LP3 | 326 | 726 | 612 | 610 | 625 | 660 |
| *Lactobacillus rhamnosus* CBT LR5 | 255 | 735 | 621 | 622 | 621 | 612 |
| *Bifidobacterium longum* CBT BG7 | 330 | 722 | 650 | 680 | 640 | 650 |
| *Bifidobacterium lactis* CBT BL3 | 436 | 729 | 610 | 615 | 610 | 620 |
| *Bifidobacterium bifidum* CBT BF3 | 302 | 715 | 670 | 680 | 587 | 650 |
| *Streptococcus thermophilus* CBT ST3 | 310 | 712 | 660 | 620 | 600 | 668 |
| *Pediococcus pentosaceus* CBT SL4 | 346 | 732 | 680 | 655 | 670 | 680 |

Experimental Example 3: Experimental for Selection of Nitrogen Source

As shown in Table 5 below, 2 parts by weight of each nitrogen source was added to 100 parts by weight of BL broth, thereby preparing media.

TABLE 5

| Strain name | Control (BL broth) | Yeast extract | Nonfat dry milk | Isolated soy protein |
|---|---|---|---|---|
| *Lactobacillus casei* CBT LC5 | 0% | 2% | 2% | 2% |
| *Lactobacillus plantarum* CBT LP3 | 0% | 2% | 2% | 2% |
| *Lactobacillus rhamnosus* CBT LR5 | 0% | 2% | 2% | 2% |
| *Bifidobacterium longum* CBT BG7 | 0% | 2% | 2% | 2% |
| *Bifidobacterium lactis* CBT BL3 | 0% | 2% | 2% | 2% |
| *Bifidobacterium bifidum* CBT BF3 | 0% | 2% | 2% | 2% |
| *Streptococcus thermophilus* CBT ST3 | 0% | 2% | 2% | 2% |
| *Pediococcus pentosaceus* CBT SL4 | 0% | 2% | 2% | 2% |

0.1 to 1 part by weight of each starter culture was inoculated into 100 parts by weight of each prepared medium, and then cultured for 20 hours while the pH was maintained at about 5.0 to 6.5. Next, the viable cell count of each culture was measured, and the results of the measurement are summarized in Table 6 below. As a result, it was confirmed that culture with yeast extract or isolated soy protein exhibited a better effect on the growth of the lactic acid bacteria than the other nitrogen sources. Thus, yeast extract or isolated soy protein was selected for a subsequent experiment (Table 6).

TABLE 6

(unit: ×10⁷ cfu/ml)

| Strain name | Control (BL broth) | Yeast extract | Nonfat dry milk | Isolated soy protein |
|---|---|---|---|---|
| *Lactobacillus casei* CBT LC5 | 355 | 670 | 560 | 680 |
| *Lactobacillus plantarum* CBT LP3 | 325 | 820 | 615 | 885 |
| *Lactobacillus rhamnosus* CBT LR5 | 226 | 750 | 645 | 890 |
| *Bifidobacterium longum* CBT BG7 | 342 | 752 | 670 | 725 |
| *Bifidobacterium lactis* CBT BL3 | 442 | 815 | 775 | 806 |
| *Bifidobacterium bifidum* CBT BF3 | 301 | 670 | 604 | 770 |
| *Streptococcus thermophilus* CBT ST3 | 295 | 620 | 805 | 720 |
| *Pediococcus pentosaceus* CBT SL4 | 315 | 722 | 715 | 780 |

Experimental Example 4: Experiment for Combination of Nitrogen Sources

As shown in Table 7 below, yeast extract and isolated soy protein were mixed together at the indicated ratios, and then 2 parts by weight of each mixture was added to 100 parts by weight of BL broth, thereby preparing media.

TABLE 7

| Strain name | Control (BL broth) | 1:1 50%:50% | 1:2 33%:67% | 1:3 25%:75% | 2:1 67%:33% | 3:1 75%:25% |
|---|---|---|---|---|---|---|
| Lactobacillus casei CBT LC5 | 0% | 2% | 2% | 2% | 2% | 2% |
| Lactobacillus plantarum CBT LP3 | 0% | 2% | 2% | 2% | 2% | 2% |
| Lactobacillus rhamnosus CBT LR5 | 0% | 2% | 2% | 2% | 2% | 2% |
| Bifidobacterium longum CBT BG7 | 0% | 2% | 2% | 2% | 2% | 2% |
| Bifidobacterium lactis CBT BL3 | 0% | 2% | 2% | 2% | 2% | 2% |
| Bifidobacterium bifidum CBT BF3 | 0% | 2% | 2% | 2% | 2% | 2% |
| Streptococcus thermophilus CBT ST3 | 0% | 2% | 2% | 2% | 2% | 2% |
| Pediococcus pentosaceus CBT SL4 | 0% | 2% | 2% | 2% | 2% | 2% |

0.1 to 1 part by weight of each starter culture was inoculated into 100 parts by weight of each prepared medium, and then cultured for 20 hours while the pH was maintained at about 5.0 to 6.5. Next, the viable cell count of each culture was measured, and the results of the measurement are summarized in Table 8 below. As a result, it was confirmed that culture with yeast extract and isolated soy protein at a mixing ratio of 3:1 (75%: 25%) exhibited a better effect on the growth of the lactic acid bacteria than culture at the other mixing ratios. Thus, the mixing ratio of 3:1 was selected as a mixing ratio for a subsequent experiment (Table 8).

TABLE 8

(unit: $\times 10^7$ cfu/ml)

| Strain name | Control (BL broth) | 1:1 50%:50% | 1:2 33%:67% | 1:3 25%:75% | 2:1 67%:33% | 3:1 75%:25% |
|---|---|---|---|---|---|---|
| Lactobacillus casei CBT LC5 | 348 | 690 | 670 | 680 | 690 | 702 |
| Lactobacillus plantarum CBT LP3 | 318 | 830 | 863 | 872 | 886 | 895 |
| Lactobacillus rhamnosus CBT LR5 | 235 | 760 | 845 | 854 | 863 | 906 |
| Bifidobacterium longum CBT BG7 | 318 | 762 | 733 | 745 | 755 | 825 |
| Bifidobacterium lactis CBT BL3 | 422 | 822 | 785 | 796 | 803 | 816 |
| Bifidobacterium bifidum CBT BF3 | 317 | 702 | 725 | 734 | 752 | 802 |
| Streptococcus thermophilus CBT ST3 | 322 | 705 | 715 | 720 | 725 | 810 |
| Pediococcus pentosaceus CBT SL4 | 336 | 780 | 765 | 740 | 750 | 833 |

Experimental Example 5: Experiment for Selection of Optimal Mixture Composition Comprising Four Different Components As shown in Table 9 below, glucose, fructooligosaccharide, yeast extract and isolated soy protein were mixed together at the indicated ratios, and then 2 parts by weight of each of the mixtures was added to 100 parts by weight of BL broth, thereby preparing media.

TABLE 9

| Strain name | Control (BL broth) | 25%:25%: 25%:25% | 20%:20%: 30%:30% | 30%:30%: 20%:20% | 40%:40%: 10%:10% | 40%:40%: 15%:5% |
|---|---|---|---|---|---|---|
| Lactobacillus casei CBT LC5 | 0% | 2% | 2% | 2% | 2% | 2% |
| Lactobacillus plantarum CBT LP3 | 0% | 2% | 2% | 2% | 2% | 2% |
| Lactobacillus rhamnosus CBT LR5 | 0% | 2% | 2% | 2% | 2% | 2% |
| Bifidobacterium longum CBT BG7 | 0% | 2% | 2% | 2% | 2% | 2% |
| Bifidobacterium lactis CBT BL3 | 0% | 2% | 2% | 2% | 2% | 2% |
| Bifidobacterium bifidum CBT BF3 | 0% | 2% | 2% | 2% | 2% | 2% |
| Streptococcus thermophilus CBT ST3 | 0% | 2% | 2% | 2% | 2% | 2% |
| Pediococcus pentosaceus CBT SL4 | 0% | 2% | 2% | 2% | 2% | 2% |

0.1 to 1 part by weight of each starter culture was inoculated into 100 parts by weight of each of the prepared media, and then cultured for 20 hours while the pH was maintained at about 5.0 to 6.5. Next, the viable cell count of each culture was measured, and the results of the measurement are summarized in Table 10 below. As a result, it was confirmed that, as the content of the carbon source was higher than the content of the nitrogen source, the effect of the carbon source and the nitrogen source on the growth of the lactic acid bacteria increased, and when 40 wt % glucose, 40 wt % fructooligosaccharide, 15 wt % yeast extract and 5 wt % isolated soy protein were mixed together, the mixture exhibited the best effect on the growth of the lactic acid bacteria.

TABLE 10

(unit: ×10$^7$ cfu/ml)

| Strain name | Control (BL broth) | 25%:25%: 25%:25% | 20%:20%: 30%:30% | 30%:30%: 20%:20% | 40%:40%: 10%:10% | 40%:40%: 15%:5% |
|---|---|---|---|---|---|---|
| Lactobacillus casei CBT LC5 | 344 | 770 | 760 | 820 | 970 | 1,070 |
| Lactobacillus plantarum CBT LP3 | 334 | 746 | 735 | 810 | 935 | 1,040 |
| Lactobacillus rhamnosus CBT LR5 | 243 | 762 | 732 | 832 | 975 | 1,030 |
| Bifidobacterium longum CBT BG7 | 312 | 740 | 725 | 825 | 925 | 1,050 |
| Bifidobacterium lactis CBT BL3 | 419 | 730 | 720 | 760 | 910 | 1,100 |
| Bifidobacterium bifidum CBT BF3 | 305 | 700 | 710 | 840 | 922 | 1,020 |
| Streptococcus thermophilus CBT ST3 | 345 | 680 | 700 | 752 | 912 | 1,120 |
| Pediococcus pentosaceus CBT SL4 | 332 | 775 | 732 | 796 | 948 | 1,050 |

Experimental Example 6: Experiment for Verification of Optimal Mixture Composition To finally verify the effect of the optimal mixture composition, mixtures of two or three of the four components were compared with the final mixture composition. As shown in Table 11 below, glucose, fructooligosaccharide, yeast extract and isolated soy protein were mixed together at various ratios as follows: Comparative Example 1 (not comprising), Comparative Example 2 (75% yeast extract and 25% isolated soy protein), Comparative Example 3 (80% glucose, 15% yeast extract, and 5% isolated soy protein), Comparative Example 4 (80% fructooligosaccharide, 15% yeast extract, and 5% isolated soy protein), and Example (40% glucose, 40% fructooligosaccharide, 15% yeast extract, and 5% isolated soy protein). Then, 2 parts by weight of each of the mixtures was added to 100 parts by weight of BL broth, thereby preparing media.

0.1 to 1 part by weight of each starter culture was inoculated into 100 parts by weight of each of the prepared media, and then cultured for 20 hours while the pH was maintained at about 5.0 to 6.5. Next, the viable cell count of each culture was measured, and the results of the measurement are summarized in Table 12 below. In addition, the growth curve of each strain was analyzed by measuring the number of viable cells at 2-hour intervals for 20 hours (FIGS. 1 to 4). As a result, it was confirmed that culture with the composition of the Example (the composition comprising the mixture of glucose, fructooligosaccharide, yeast extract and isolated soy protein) exhibited an excellent effect of promoting the growth of all the eight types of lactic acid bacteria compared to culture with each of the compositions of Comparative Examples 1 to 4, and it could be confirmed that the composition of the Example exhibited not only the effects of activating the growth of the lactic acid bacteria and promoting cell division, but also the stability effect of allowing the proliferated lactic acid bacteria to survive for a long time (Table 12 and FIGS. 1 to 4).

TABLE 11

| Strain name | Comparative Example 1 (not comprising) | Comparative Example 2 | Comparative Example 3 | Comparative Example 4 | Example |
|---|---|---|---|---|---|
| Lactobacillus casei CBT LC5 | 0% | 2% | 2% | 2% | 2% |
| Lactobacillus plantarum CBT LP3 | 0% | 2% | 2% | 2% | 2% |
| Lactobacillus rhamnosus CBT LR5 | 0% | 2% | 2% | 2% | 2% |
| Bifidobacterium longum CBT BG7 | 0% | 2% | 2% | 2% | 2% |
| Bifidobacterium lactis CBT BL3 | 0% | 2% | 2% | 2% | 2% |
| Bifidobacterium bifidum CBT BF3 | 0% | 2% | 2% | 2% | 2% |
| Streptococcus thermophilus CBT ST3 | 0% | 2% | 2% | 2% | 2% |
| Pediococcus pentosaceus CBT SL4 | 0% | 2% | 2% | 2% | 2% |

TABLE 12

(unit: ×10⁷ cfu/ml)

| Strain name | Comparative Example 1 (not comprising) | Comparative Example 2 | Comparative Example 3 | Comparative Example 4 | Example |
|---|---|---|---|---|---|
| *Lactobacillus casei* CBT LC5 | 363 | 702 | 715 | 722 | 1,040 |
| *Lactobacillus plantarum* CBT LP3 | 327 | 895 | 920 | 915 | 1,030 |
| *Lactobacillus rhamnosus* CBT LR5 | 252 | 906 | 935 | 944 | 1,050 |
| *Bifidobacterium longum* CBT BG7 | 316 | 825 | 837 | 872 | 1,050 |
| *Bifidobacterium lactis* CBT BL3 | 399 | 816 | 845 | 882 | 1,090 |
| *Bifidobacterium bifidum* CBT BF3 | 312 | 802 | 822 | 850 | 1,070 |
| *Streptococcus thermophilus* CBT ST3 | 317 | 810 | 825 | 838 | 1,040 |
| *Pediococcus pentosaceus* CBT SL4 | 343 | 833 | 826 | 872 | 1,000 |

As described in detail above, the composition for promoting the growth of lactic acid bacteria comprising growth factors according to the present disclosure may promote the growth of lactic acid bacteria, and thus may be used universally as a composition for promoting the growth of various lactic acid bacteria.

Although the present disclosure has been described in detail with reference to the specific features, it will be apparent to those skilled in the art that this description is only of a preferred embodiment thereof, and does not limit the scope of the present disclosure. Thus, the substantial scope of the present disclosure will be defined by the appended claims and equivalents thereto.

[Accession Number]
Depository authority: Korea Research Institute of Bioscience and Biotechnology
Accession number: KCTC12199BP
Deposit date: Apr. 27, 2012
Depository authority: Korea Research Institute of Bioscience and Biotechnology
Accession number: KCTC12200BP
Deposit date: Apr. 27, 2012
Depository authority: Korea Research Institute of Bioscience and Biotechnology
Accession number: KCTC11904BP
Deposit date: Mar. 30, 2011
Depository authority: Korea Research Institute of Bioscience and Biotechnology
Accession number: KCTC12398BP
Deposit date: Apr. 5, 2013
Depository authority: Korea Research Institute of Bioscience and Biotechnology
Accession number: KCTC10782BP
Deposit date: Mar. 16, 2005
Depository authority: Korea Research Institute of Bioscience and Biotechnology
Accession number: KCTC12202BP
Deposit date: Apr. 27, 2012
Depository authority: Korea Research Institute of Bioscience and Biotechnology
Accession number: KCTC10297BP
Deposit date: Jun. 25, 2002
Depository authority: Korea Research Institute of Bioscience and Biotechnology
Accession number: KCTC11870BP
Deposit date: Feb. 17, 2011

What is claimed is:

1. A method for promoting the growth of lactic acid bacteria, the method comprising culturing the lactic acid bacteria in a medium;
wherein the medium comprises glucose, fructooligosaccharide, yeast extract and isolated soy protein, wherein the weight ratio of the glucose and the fructooligosaccharide is 1:1, and wherein a weight ratio of the yeast extract and the isolated soy protein is 3:1.

2. The method of claim 1, wherein the lactic acid bacteria is selected from at least one group consisting of *Lactobacillus casei, Lactobacillus plantarum, Lactobacillus rhamnosus, Bifidobacterium longum, Bifidobacterium lactis, Bifidobacterium bifidum, Streptococcus thermophilus* and *Pediococcus pentosaceus*.

* * * * *